United States Patent [19]

Clements

[11] 4,312,860
[45] Jan. 26, 1982

[54] LUNG SURFACTANT COMPOSITIONS

[75] Inventor: John A. Clements, Tiburon, Calif.

[73] Assignee: Regents of the University of California, Berkeley, Calif.

[21] Appl. No.: 200,216

[22] Filed: Oct. 24, 1980

[51] Int. Cl.³ .............................................. A01N 57/26
[52] U.S. Cl. ..................................................... 424/199
[58] Field of Search ......................................... 424/199

[56] References Cited

U.S. PATENT DOCUMENTS 3,577,446  5/1971  Rakmit ................................. 424/199
4,129,650 12/1978  Betzing et al. ...................... 424/199

Primary Examiner—Elbert L. Roberts
Attorney, Agent, or Firm—Phillips, Moore, Weissenberger, Lempio & Majestic

[57] ABSTRACT

A synthetic protein-free lung surfactant composition is utilized to temporarily substitute for natural lung surfactant in the mammalian lung where such natural lung surfactant is absent or in low concentration. The synthetic surfactant composition consists essentially of a major amount of 1,2-dipalmitoyl-sn-3-glycerophosphoryl choline (DPPC), and a minor amount of a fatty alcohol, preferably a fatty alcohol having from 14 to 18 carbon atoms, and especially n-hexdecan-1-ol. The synthetic surfactant composition is administered directly into the lungs of a distressed subject to create a film on the alveolar interfacial surfaces and reduce surface tension. Expansion of the alveolar spaces is thereby facilitated.

9 Claims, No Drawings

LUNG SURFACTANT COMPOSITIONS

The invention described herein was made in the course of, or under, a grant from the National Institutes of Health.

DESCRIPTION

BACKGROUND OF THE INVENTION

The present invention is directed to compositions useful in alleviating the symptoms of mammalian respiratory distress syndrome (RDS) which may occur in the newborn, and especially in the prematurely newborn, as well as, in many instances in the adult when disease or functional difficulties bring about lung failure characterized by the deficiency of lung surfactant. The invention compositions may be introduced into the lungs of the distressed subject to temporarily provide the surfactant required for proper pulmonary function.

In the past several decades, the findings and writings of a number of investigators have brought greatly increased understanding in the medical community of the physiology of the mammalian lung; especially pertaining to the mechanisms involved in the transfer of gases from the air spaces in the lungs across the lining tissues to the underlying vascular system. These studies have revealed the critical role played by a liquid film which lines the tissue surfaces. This role is based upon basic physical principles which have been known for several hundred years, but whose application to the operation of the mammalian lung has only reached general recognition within the past 20 years or so.

Specifically, the basic physics principles involve the functioning of surface tension, i.e., the physical phenomenon exhibited by liquid surfaces brought about by intermolecular forces and resulting in a "skin like" effect. This phenomenon underlies the tendency of the lung's air sacs, or alveoli, to expell gas at all times during the respiratory cycle. If sufficiently low surface tension forces are not maintained at the air-lung tissue interface, the alveoli collapse during exhalation. Even the inspiration of air through the bronchi may be ineffective in inflating the collapsed alveoli and gas exchange into the pulmonary circulatory system may be inadequate.

Establishing and maintaining low surface tension at the alveolar surfaces is accomplished by an intricate biological system associated with alveolar lung tissue. Special cells, known as alveolar Type II, synthesize a complex mixture of lipids, proteins, glycerides and fatty acids. This complex is stored in the form of lamellar bodies within the alveolar Type II cells. By a mechanism little understood, the lamellar bodies are extruded from the alveolar Type II cells into alveolar lumen where the lamellae unwind and distribute the lipid, protein, glyceride, etc. molecules throughout the liquid film which bathes the entire cellular covering of the alveolar walls. These molecules, which may be generically referred to as "lung surfactant," migrate to the surface of the liquid film where they produce an essentially mono-molecular, all pervasive layer thereon.

The surfactant, effectively lowers the surface tension of the film to low values (circa 10 millineutons/meter) sufficient to maintain alveolar inflation during all phases of the respiratory cycle.

The chemical composition of "lung surfactant" has been investigated and the results have been published in a number of papers, e.g. Respiratory Distress Syndrome, *Academic Press Inc.*, 1973, pp. 77–98. Such studies indicate that natural lung surfactant is a complex mixture of many components of which the major component is a lipid, dipalmitoyl phosphatidyl choline (according to current naming criteria more correctly, 1,2-dipalmitoyl-sn-3-glycerophosphoryl choline). Dipalmitoyl phosphatidyl choline, commonly abbreviated as DPPC, occurs in lung surfactant to the extent of about 41% by weight. Mixed monenoic lecithins make up about 25% by weight; cholesterol makes up about 9% by weight; mixed proteins about 9% by weight; phosphatidyl ethanolamine, about 5%; various glycerides and phosphatidyl serine and phosphatidyl glycerol, about 4%, respectively; lysolecithin, about 2%; with sphingomyelin and fatty acids, each about 1%. The above noted materials and %'s are for surfactant removed from canine lungs; however, the mix of materials and %'s generally hold true for the higher mammals. For instance, both bovine and human lung surfactant also comprise a similar mix, with DPPC running in the same range of approximately 40% by weight.

Respiratory distress syndrome occurs when the necessary surfactant is either absent from, or is seriously depleted in, the liquid lining of the alveolar spaces. The most common occurrance is in the newborn and especially in the premature newborn, wherein development of the alveolar Type II cells has not yet arrived at a stage sufficient to generate the necessary surfactant material. The maturation of the alveolar Type II cells normally occurs within the last several weeks of full term gestation. However, in some instances congenital defects interfere with and/or delay maturation of the alveolar Type II cells; or more commonly in the instance of premature birth, maturation has not yet progressed sufficiently to generate the necessary surfactant.

In other instances, interruption of the generation of surfactant may occur in the mature and/or adult individual under the impact of disease and/or trauma.

It will be apparent from what has been noted herein and before that the lack of maturation of the surfactant generating mechanisms in the newborn and especially in the prematurely newborn, or the interruption of the surfactant generating mechanism resulting from disease or trauma, will result in the absence or the diminution of the necessary surfactant on the lining of the alveolar spaces. The absence of the necessary surfactant eliminates or may drastically interfer with the ability of the newborn lung to properly inflate as respiration begins. Similarly, collapse or deflation of the alveolar spaces occurs in the mature lung when the supply of surfactant is interrupted or diminished because of disease or trauma.

The absence or loss of lung surfactant is manifest by severe respiratory distress, which if not managed by medical intervention may most usually result in death. In the past, such medical intervention included such measures as supplying high levels of oxygen; positive pressure application to the lungs to provide adequate pulmonary ventilation; adequate attention to the maintenance of nutrition, fluid balance, blood volume, and blood pressure etc. In addition, in the case of the premature newborn it has been determined that the introduction of corticosteroids actively induces rapid maturation of the natural surfactant production system. Such steroid therapy, however, must be undertaken before the actual premature birth occurs in order to be truly effective in achieving early maturation of the surfactant producing systems. With recent techniques of analyzing amniotic fluids, tests have been devised for determining the presence of adequate amounts of surfactant in the unborn fetus. Where it is anticipated that a premature birth will occur, such tests can be performed and if inadequate levels of surfactant are noted, steroid therapy can be instituted to hasten the maturation of the natural surfactant production systems.

Rather fortuitously soon after birth the corticosteroid systems begin and/or increase production of the corticosteroids internally and if the individual can be maintained for relatively short periods of time, in the matter of several days, maturation of the surfactant production systems will occur. Under these circumstances sufficient surfactants will soon be released into the alveolar surfaces to produce the low surface tension necessary to the full and unassisted expansion to maintain normal respiratory function.

Therefore, it becomes extremely critical to somehow manage the respiratory distress for a relatively short period of time (normally for a period of several days) until the natural systems can come into play and take over their role in maintaining a normal expansion of the alveolar spaces.

As pointed out above, in the past, management has included positive pressure pulmonary ventilation along with the monitoring and maintenance of secondary functions. However, with the discovery of the nature of lung surfactant, some work has been done to replace the lacking surfactant with exogenous surfactant components. Generally speaking, however, such attempts have been unsuccessful until Fujiwara and his coworkers used cow lung extract fortified with DPPC and phosphatidylglycerol, two of the principal components of natural lung surfactant. Fujiwara, et al. reported their work in Lancet 1:55, January 1980.

One of the possible shortcomings of a substitute surfactant derived from animal lung extracts are its undefined nature, the possibility of contamination with micro-organisms, and especially the presence of foreign proteins which may lead to possible sensitization in the individual to whom such extracts are administered. It is therefore desirable to develop a lung surfactant substitute whose composition is completely defined, whose production may essentially exclude any possibility of microbial contamination, and in which, antigenic proteins are completely absent.

With regard to the preparation of artificial lung surfactant compositions which are free of protein, I. L. Metcalfe and his coworkers have reported (J. Applied Physiology: Respiratory Environmental Exercise Physiology 49:34, 1980) that a composition of 70% DPPC, 20% egg phosphatidylcholine, 10% phosphotidylinositol and 1% palmitic acid, exhibits acceptable properties. Similarly, C. J. Morley at the 16th International Congress of Pediatrics held at Barcelona, September 1980 reported that an artificial surfactant consisting of DPPC and unsaturated phosphatidylglycerol shows promise.

Despite the reports of synthetic surfactant noted above, the preparation of a protein free synthetic lung surfactant substitute suitable as a temporary replacement for natural lung surfactant has been quite difficult since the physiochemical characteristics of natural lung surfactant are complex and at times contradictory. The principal characteristics of a lung surfactant are (1) it must absorb very rapidly from bulk phase to the liquid interface lining the alveolar tissues and spread a film thereon. The film must be formed rapidly since newborns have a high respiratory rate and only a few tenths of a second is available during inspiration to form the film while the air spaces are expanding. (2) The surfactant surface film must be stable to ensure that the surface tension remains at a low value (not more than 10 mN/m) during expiration. The stable film ensures that as transpulmonary pressure falls, the alveolar spaces remain expanded and functional; and that residual volume does not decrease to zero. (3) Although some of the surfactant material inevitably is forced from the interfacial film during expiration, it is essential that the surfactant have sufficient mobility to reenter the interface during the next expansion. Such properties of the surfactant ensures that its loss from the interfacial film is not so high as to require excessive dosage volumes and/or rates.

Some of the requirements for the surfactants as noted above, appear to be contradictory insofar as the physicochemical properties of the lung surfactant materials are concerned. Thus, the high molecular mobility required for rapid adsorption and respreading into the interfacial film contradicts the low mobility necessary for a stable and persistent film. In natural lung surfactant, this contradiction is apparently resolved through the complexity of the multicomponents as noted above which are organized around a specific protein. Such complex material apparently has the ability to spontaneously undergo the necessary molecular sorting and phase changes required to satisfy these apparently contradictory physico chemical requirements. Thus the preparation of a simple, yet effective synthetic lung surfactant appears to be fought with difficulty.

BRIEF SUMMARY OF THE INVENTION

The present invention is broadly concerned with synthetic lung surfactant compositions and more specifically with simple, easily and inexpensively prepared surfactant compositions which are free from proteins, are made from known components securable from common industrial sources.

The synthetic lung surfactant compositions consist essentially of two components, more particularly, with synthetic lung surfactant compositions derived from mixtures of dipalmitoyl phosphatidylcholine and fatty alcohols. The dipalmitoyl phosphatidylcholine (DPPC) constitutes the major component of the surfactant composition while the fatty alcohol comprises a minor component thereof. The fatty alcohol component of the compositions may be any of a number of fatty alcohols having from 14-18 carbon atoms and may be either saturated or unsaturated. The much preferred fatty alcohol, however, is hexadecanol i.e. n-hexadecan-1-ol. Unsaturated fatty alcohols such as oleic alcohol may also be utilized in the surfactant compositions. Other fatty alcohols may also be utilized so long as they satisfy the criteria for the synthetic lung surfactant composition as noted above.

Suspensions of the synthetic lung surfactant are utilized for the treatment for respiratory distress syndrome in mammals by administering suspensions (aqueous or saline) of the surfactant directly into the lungs of the distressed subject.

Both DPPC and the fatty alcohol component are substances which occur naturally in mammalian tissues, although they do not occur together as a specific moiety. DPPC in fact occurs as the principal component in natural lung surfactant; however, the fatty alcohols of the present composition are not known to occur naturally in lung tissue. Since both components of the surfactant composition do occur naturally within mammalian tissues, they are also metabolizable and their eventual elimination from a subject is accomplished by normal processes. Similarly, the hazard associated with the introduction into the organism of foreign substances is of no consideration with the present compositions.

DETAILED DESCRIPTION OF THE INVENTION

The synthetic lung surfactant compositions of this invention are protein-free and consist essentially of two components. The major component is dipalmitoyl phosphatidyl choline (DPPC), which is also the major component of naturally occurring lung surfactant. DPPC has been synthesized in the laboratory. It is a lipid, i.e., one of the broad class of organic compounds found in cells which are extractable by nonpolar solvents such as chloroform, ether, and benzene. It is comprised of two palmito-moieties linked to the phospho-glyceride moiety, phosphatidyl choline. The simple structural formula may be depicted as:

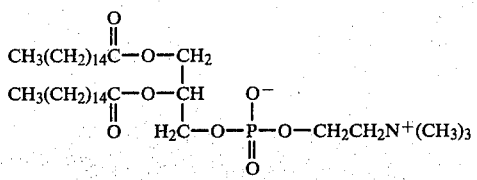

The lipid may be obtained in high purity on the commercial market.

The dipalmitoyl phosphatidyl choline is an essential component of the synthetic surfactant compositions and accounts for some of the desired properties of lung surfactant i.e., it forms very stable monolayers at 37° C., and is a principal component of natural lung surfactant. DPPC may be present in the synthetic compositions over a fairly wide range, although in any event as the major component. It has been tested at a percentage of as low as 82%, and as high as 94% by weight with no noted change in the surfactant's in vitro properties. Generally, however, DPPC is preferred in about 90% by weight in the surfactant composition.

The second component of the synthetic surfactant compositions is a fatty alcohol having carbons in the range of from about 14 to 18. Such fatty alcohols may be either saturated or unsaturated, although the saturated alcohol, hexadecanol (n-hexadecan-1-ol) is greatly preferred. The unsaturated alcohol, oleic alcohol, has also been combined with DPPC and the resultant surfactant appears to have the necessary properties.

Any of the closely related fatty alcohols in the C-14 to C-18 range can also be utilized so long as the resultant surfactant composition satisfies the required properties enumerated in the background section above.

The fatty alcohols are available in high purity on the commercial market. The alcohol component constitutes a minor portion of the surfactant composition, being present in an amount ranging from about 5 or 6% to about 18% or 20% by weight of the composition. The preferred composition of the synthetic surfactants of the invention is DPPC in about 90% by weight and hexadecanol in about 10% by weight. However, the percentages may be altered as noted above without unduly interfering with the desired properties.

The synthetic lung surfactant compositions of the invention are simple mixtures of the dipalmitoyl phosphatidyl choline component and the fatty alcohol component. Preparation and storage of the surfactant composition may best be understood by reference to the examples set forth below.

EXAMPLE I

Synthetic lung surfactant was prepared from chromatographically pure (greater than 99%), dipalmitoyl phosphatidyl choline and hexadecanol. Both materials were purchased on the commercial market where they are available from a number of chemical supply houses. Specifically, DPPC was purchased from both the Fluka Company and Sigma Chemical Company. Hexadecanol was purchased from NuChek Prep. Company. All of the purchased materials were checked for purity by chromatographic analysis.

The lung surfactant composition was prepared as follows: 314 mg. of DPPC and 33.6 mg. of hexadecanol were dissolved in 10 ml. of 1/1 chloroform/methanol (V/V, C.P.). The dissolved materials were then transferred to a 1000 ml round bottom flask. The flask was attached to a rotary vacuum evaporator and the chloroform/methanol solvent was evaporated at 37° C. leaving the synthetic surfactant lipids in a dry, thin film on the lower half of the wall of the flask. A number of clean glass beads (5 mm diameter) and 5 ml of saline were introduced in to the flask. The flask was then stoppered and the beads were then circulated by hand by swirling until all of the lipid residue had been stripped from the wall and dispersed throughout the saline solution. The dispersing procedure was carried out at 50°–52° C. by warming under running tap water. After the initial suspension of the lipids in saline an additional 18 ml of saline was added to make a total volume of 23 ml. The resultant suspension had a concentration of about 15 mg. of lung surfactant per ml. The suspension was transferred to a 30 ml syringe for dispensing.

Upon standing the suspension settled in about 5 minutes, but it could be readily redispersed by swirling even after a week of storage at 5° C. The suspension is capable of being preserved indefinitely when frozen at −70° C.

A portion of the above-noted preparation was re-suspended in distilled water to check its properties. The appearance of the suspension was like that in saline i.e. it was pure white in color, had no taste or odor and was completely bland and nonirritating to the tongue and mucus membranes of the mouth and nose.

EXAMPLE II

In an alternate method the synthetic lung surfactant may be prepared according to the following:

Synthetic 1,2 dipalmitoyl-sn-3 glycerophosphorylcholine (99% pure) (DPPC) may be obtained from Sigma Co., St. Louis, Mo. or Applied Science Labs. State College, Pa. and checked by thin layer and gas-liquid chromatography for contaminants and degradation products. It can be used only if it is at least 99% pure by chromatography. Phosphorus must be between 3.9 and 4.1% by weight. Specific rotation should be $\alpha_{20}{}^D + 5.7°$ (10% in chloroform).

Synthetic n-hexadecan-1-ol (>99% pure) may be obtained from Nu Chek Prep Co., Elysian, Minn., and checked by gas-liquid chromatography for other fatty alcohols. It is acceptable if it contains not more than 1% of other fatty alcohols.

DPPC and the fatty alcohol are dissolved in a ratio of 9:1 by weight in redistilled chloroform to give a solution containing 1.125 grams total in 20 ml. This solution is placed in a sterile Virtis 150 ml lyophilization flask and the chloroform completely removed by rotary vacuum evaporation so as to deposit the lipids in a film on the bottom one third of the flask. 100 ml of sterile 0.10 N sodium chloride (SUP) solution is added and the lipids suspended by intermittent sonication (Branson sonifier 185, large probe, scale setting 50) at room temperature until the suspension is uniform to inspection. Care must be taken that the temperature of the solution does not exceed 35° C. Half of this solution is then shelled (frozen) on the wall of each of two sterile 300 ml Virtis flasks, using a dry-ice alcohol bath, and subsequently lyophilized. The residue containing 802 mg. surfactant and 421 mg. sodium chloride, total weight 1,224 mg. in each flask is pulverized with a spatula and then transferred to 7 sterile 10 ml. vacuum vials, 175 mg. of pulverized product in each. The vials are evacuated and stoppered with vacuum-tight rubber seals, with a Virtis apparatus, and capped. The vials may be stored at 5° C. or below until needed.

Administration of the Lung Surfactant Compositions

The compositions, prepared as noted in Examples I and II above, are intended for administration directly into the lungs of the distressed subject.

In the case of preparation according to Example I, the frozen composition is allowed to warm to ambient temperature, at which time, the lipids are redispersed in the saline medium by swirling. The redispersed compositions and saline are then simply introduced directly into the lungs via an endotracheal tube. A dose rate of about 7.5 ml./kg. (112 mg./kg.) of subject body weight is adequate.

In the case of the preparation according to Example II, it has already been noted that the material is redispersed shortly before use. More specifically, 15 minutes before use, the material is reconstituted with 10 ml. distilled water. A kit is provided which contains:
1 vial of surfactant, 115 mg.-sodium chloride 60 mg.;
1 ampoule of sterile distilled water, 15 ml. and an ampoule knife;
1 30 ml. disposable syringe, 3-way stopcock, and two 20 gage needles;
1 alcohol gauze pad, 2×2;
A tank of medical grade oxygen is to be available.

The vacuum vial is uncapped and the rubber seal cleaned with alcohol. The ampoule is cleaned, scored, and opened and 10 ml of the distilled water aspirated into the 30 ml. syringe. The seal of the vaccum vial is punctured so that the distilled water is drawn into the surfactant. A second 20 gage needle is introduced through the seal, so that the suspension of surfactant can be passed vigorously at least 5 times between the vial and the syringe and finally into the syringe. 10 ml. of oxygen is drawn in, via the side port of the stopcock.

When the subject's weight is known, the suspension is re-mixed and all but 7 ml./kg. is expelled into the vial. The stop cock is closed. The remainder, containing 80 mg. surfactant/kg. (about 15 times the normal amount of alveolar DPPC), is shaken well in the syringe with the oxygen. Suspension, foam, and oxygen are administered via a cuffed endotracheal tube and followed by vigorous resuscitation.

Testing

The synthetic surfactant compositions are tested both in vitro and in vivo. Of course, several requirements of the synthetic surfactant compositions are inherently satisfied because of the components themselves. Specifically, since the DPPC and fatty alcohol are secured from sources which have synthesized the components and the components are tested for assured purity, no proteins are present in the compositions. Thus the chance of antibody reaction by the treated subject is eliminated. Secondly, since the components have not been derived from animal sources, there is essentially no chance for contamination by bacteria or viruses. Thirdly, since the components are secured in a highly pure state, it is easy to prepare standardized and therefore reproducible mixtures from batch to batch of surfactant. Thus, quality control is greatly simplified. Finally, since both components occur naturally, although not associated, within animal tissues, metabolic pathways for eventual elimination are already established and there is no introduction into the subject of biologically foreign substances.

As to the specific properties required of such surfactant compositions and set forth hereinbefore, a relatively simple in vitro test has been devised. This test is a "shake test" modified from a procedure devised by the present inventor for the purpose of testing for natural surfactant in amniotic fluid. This test was originally disclosed in the New England Journal of Medicine 286 pp. 1077–1081, 1972.

The test is as follows:

A sample of the carefully mixed synthetic surfactant composition prepared according to Example II containing about 400 micrograms of the surfactant is placed in a 20 ml. culture tube. 2 ml. of saline is added, and the tube is tightly capped with a screw cap. The capped tube is immersed in a water bath held at 37° C. for a time (5 minutes) sufficient to equilibrate the temperature of the sample with that of the bath. The tube is then removed and shaken vigorously by hand for 15 seconds and then replaced into the bath.

The presence of a copious foam at the meniscus confirms that the surfactant components are absorbed from the liquid phase into the surface and create a film thereon. If the bubbles are tiny and remain for 15 minutes or more, the test confirms that the surface film is stable and maintains a low surface tension.

All samples prepared according to the invention compositions, passed the "shake test". Although the test is quite simple, it has been shown to correctly assay several of the properties required by lung surfactant compositions.

The surfactant compositions may also be tested in vivo on prematurely delivered lambs at 120–130 days gestation. At this stage of gestation endogenous lung surfactant is absent and respiratory function is inadequate.

When a 90% DPPC-10% hexadecanol suspension was introduced directly into the bronchi at a dosage of approximately 90 mg/kg of body weight, subsequent arterial blood analysis indicated good $CO_2$ and $O_2$ exchange. Rapid lung expansion was also noted.

I claim:

1. A mammalian lung surfactant composition consisting essentially of dipalmitoyl phosphatidylcholine in admixture with a fatty alcohol.

2. The composition of claim 1 wherein the fatty alcohol has from about 14 to 18 carbon atoms.

3. The composition of claim 2 wherein the fatty alcohol is hexadecanol.

4. The composition of claim 2 wherein the fatty alcohol is oleic alcohol.

5. The composition of claim 1 wherein the dipalmitoyl phosphotidyl choline constitutes a major percentage by weight of the composition and wherein the fatty alcohol constitutes a minor percentage.

6. The composition of claim 5 wherein the fatty alcohol is present in the range of about 6 to 18% by weight and the dipalmitoyl phosphatidyl choline is present in the range of about 82 to 94% by weight.

7. A composition for administration into mammalian alveolar spaces comprising a suspension of dipalmitoyl phosphatidyl choline and hexadecanol in saline solution.

8. A method for treating respiratory distress syndrome in mammals wherein natural lung surfactant normally produced by the mammal is absent or deficient, comprising introducing into the alveolar spaces a quantity of a composition consisting essentially of a major amount of 1,2 dipalmitoyl-sn-3-glycerophosphoryl choline in admixture with a minor amount of a fatty alcohol.

9. The method of claim 8 wherein the fatty alcohol is n-hexadecan-1-ol.

* * * * *

UNITED STATES PATENT AND TRADEMARK OFFICE

CERTIFICATE EXTENDING PATENT TERM
UNDER 35 U.S.C. 156

Patent No.     : 4,312,860

Dated          : January 26, 1982

Inventor(s)    : John A. Clements

Patent Owner   : The Regents of The University
                 of California

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of 1,030 DAYS with all rights pertaining thereto as provided by 35 U.S.C. 156 (b).

I have caused the seal of the Patent and Trademark Office to be affixed this 30th day of December 1991.

Harry F. Manbeck, Jr.
Assistant Secretary and Commissioner
of Patents and Trademarks